United States Patent
Galant et al.

(10) Patent No.: US 7,773,719 B2
(45) Date of Patent: Aug. 10, 2010

(54) MODEL-BASED HEART RECONSTRUCTION AND NAVIGATION

(75) Inventors: Adam K. Galant, Carpentersville, IL (US); Dorin Comaniciu, Princeton Junction, NJ (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 172 days.

(21) Appl. No.: 12/054,622

(22) Filed: Mar. 25, 2008

(65) Prior Publication Data
US 2008/0240337 A1 Oct. 2, 2008

Related U.S. Application Data

(60) Provisional application No. 60/896,951, filed on Mar. 26, 2007.

(51) Int. Cl.
*A61B 6/00* (2006.01)
(52) U.S. Cl. .................... 378/4; 378/8; 378/20
(58) Field of Classification Search ............ 378/8, 378/42, 4, 20
See application file for complete search history.

(56) References Cited

U.S. PATENT DOCUMENTS

| | | | |
|---|---|---|---|
| 4,878,115 A * | 10/1989 | Elion ............ 378/98.5 |
| 5,274,551 A * | 12/1993 | Corby, Jr. .......... 600/433 |
| 5,920,319 A * | 7/1999 | Vining et al. ........ 345/420 |
| 2001/0048731 A1* | 12/2001 | Nakamura et al. ...... 378/4 |
| 2002/0181646 A1* | 12/2002 | Mehldau ............... 378/8 |
| 2003/0007593 A1* | 1/2003 | Heuscher et al. ........ 378/4 |
| 2003/0018251 A1* | 1/2003 | Solomon ............ 600/427 |
| 2003/0123606 A1* | 7/2003 | Mollus et al. ......... 378/42 |
| 2003/0161436 A1* | 8/2003 | Boyd et al. ............ 378/8 |
| 2004/0081270 A1* | 4/2004 | Heuscher .............. 378/4 |
| 2005/0249327 A1* | 11/2005 | Wink et al. ............. 378/8 |
| 2006/0247544 A1* | 11/2006 | Qazi et al. ........... 600/508 |
| 2006/0262970 A1* | 11/2006 | Boese et al. .......... 382/131 |
| 2007/0055142 A1* | 3/2007 | Webler .............. 600/425 |

* cited by examiner

*Primary Examiner*—Edward J Glick
*Assistant Examiner*—Alexander H Taningco

(57) ABSTRACT

A method to obtain a patient based organ model from patient data, having steps of obtaining a computerized organ model based upon at least one data set of patients, the computerized organ model having a set of classifiers that are used to determine physical parameters of the patients heart, placing the patient in a diagnostic scanner device, taking representative data images of a patients organ while changing position of the image scan, the data images taken with ECG synchronization; and preparing the patient based organ model by evaluating the representative data images of the patients organ with the set of classifiers in the computerized organ model.

17 Claims, 3 Drawing Sheets

MODEL-BASED HEART RECONSTRUCTION AND NAVIGATION

CROSS-REFERENCE TO RELATED APPLICATIONS

The present application seeks priority to U.S. Provisional Application 60/896,951 filed Mar. 26, 2007, the entirety of which is incorporated by reference.

FIELD

Aspects of the invention relate to evaluation of the interior organs of a patient during medical evaluations. More specifically, aspects of the invention provide for minimizing radiological exposure of patients during evaluation of interior organs, such as the heart, to provide guidance for medical professionals during medical procedures, such as during catheter movement.

BACKGROUND INFORMATION

Evaluation of a patient's interior organs is necessary in instances where a patient needs surgery. Certain organs, for example, need closer evaluation during medical procedures and therefore medical professionals take extra precaution during such evaluations. Among some of the most critical evaluations conducted, heart evaluations are becoming more prevalent.

During data acquisition for medical scans several hundred images are usually recorded, such as during a heart scan, and a patient is subjected to a large dose of radiation. This is specifically the case during cardiac scans when multiple phases of the heart are recorded during C-arm rotations to attempt to capture the heart in different configurations during beating. The radiation dose provided to the patient can be justified, if data acquisition is used for critical diagnostic evaluation and no other alternatives exist. The purpose of data acquisition is to obtain a three dimensional volume data set for the patient so the medical researcher can review navigation pathways inside the heart easier (i.e. during the ablation procedure). The risks to the patient, however, must be outweighed by the benefits conferred for the analysis to occur. Many medical procedures require precision placement of the instruments like catheters or needles. For example during the treatment of the Atrial Fibrillation (a form of the heart arrhythmia) the RF (radio frequency) ablation is performed on the inner surface of the heart chamber with aid of a special ablation catheter inserted intravenously into the heart. This ablation has to be done in precise locations determined by the earlier measurement (mapping) of the electrical waveforms on the inner surface of the left atrium. The entire procedure (mapping and ablation) takes typically several hours and is performed under low-dose ("Fluoro") x-ray to aid the physician in manipulating the catheter. The other, similar example is the deployment of the pacemaker leads. There are also many examples outside the cardiology where the success of the procedure depends on the precision of placement of the instrument inside treated organ, for example for the local drug delivery.

There is a need to provide medical professionals with a classifying system that would allow the professional to view the interior structure of a patients heart to help with patient evaluation, as well as allow medical professionals the ability to navigate within a patient's heart There is a further need to provide a medical professional with the capability to evaluate a patient's heart while minimizing potential radiation exposure of the patient.

There is also a further need to provide for accurate representation of a patients heart while using technology that is adaptable to currently used apparatus by medical professionals.

SUMMARY OF THE INVENTION

It is therefore an objective of an embodiment of the present invention to provide medical professionals with the capability to evaluate the interior structure of a patient's heart to help during dynamic patient procedures.

It is a further objective of an embodiment of the present invention to provide a medical professional with the capability to evaluate a patient's heart while minimizing potential radiation exposure of the patient to assist the professional during procedures, such as installation of a catheter.

It is a still further objective of an embodiment of the present invention to provide for accurate representation of a patient's heart while using technology that is adaptable to currently used apparatus by medical professionals.

The objectives of aspects of the invention are achieved as illustrated and described. In an exemplary embodiment of the invention, a method to obtain a patient based organ model from patient data is presented, comprising obtaining a computerized organ model based upon at least one data set of patients, the computerized organ model having a set of classifiers that are used to determine physical parameters of the patients heart; placing the patient in a diagnostic scanner device, taking representative data images of a patients organ while changing position of the image scan, the data images taken with ECG synchronization, and preparing the patient based organ model by evaluating the representative data images of the patients organ with the set of classifiers in the computerized organ model.

In a further embodiment, the method is accomplished wherein a maximum of representative data images of the patient's heart taken is 30 images.

In a further embodiment, the method further comprises visually depicting the patient's organ based upon the representative data images.

In another embodiment, the method further comprises identifying artifacts in the model based upon the representative data images taken. The method may also further comprise obtaining a second set of representative data images of the patient's heart while changing position of the image scan, the data images taken with ECG synchronization to eliminate artifacts, and preparing a revised patient based organ model by evaluating the second set of representative data images of the patients organ with the set of classifiers in the computerized organ model.

In another embodiment, the method further comprises identifying a second set of artifacts in the model based upon the representative data images taken. The method may also further comprise obtaining a third set of taking representative data images of the patient's organ while changing position of the image scan, the third set of data images taken with ECG synchronization to eliminate artifacts, and preparing a second revised patient based organ model by evaluating the representative data images of the patients organ with the set of classifiers in the computerized organ model.

In another embodiment the method is accomplished such that a maximum of representative data images of the patient's heart taken is dependent upon a number of degrees of freedom of the model.

In another embodiment, a program storage device readable by machine, tangibly embodying a program of instructions executable by the machine to perform method steps to obtain a computerized organ model based upon at least one data set of patients, the computerized organ model having a set of classifiers that are used to determine physical parameters of the patients organ, placing the patient in a diagnostic scanner device, taking representative data images of a patients organ while changing position of the image scan, the data images taken with ECG synchronization, and preparing the patient based organ model by evaluating the representative data images of the patients organ with the set of classifiers in the computerized organ model.

In another embodiment the device is prepared wherein a maximum of representative data images of the patient's organ taken is 30 images.

In another embodiment the device is prepared wherein the method accomplished further comprises visually depicting the patient's organ based upon the data images.

In another embodiment the device is prepared wherein the method accomplished further comprises identifying artifacts in the model based upon the representative data images taken.

In another embodiment the device is prepared such that the method accomplished further comprises: obtaining a second set of representative data images of the patient's organ while changing position of the image scan, the data images taken with ECG synchronization to eliminate artifacts, and preparing a revised patient based organ model by evaluating the representative data images of the patients organ with the set of classifiers in the computerized organ model. A maximum of representative data images of the patients heart taken is dependent upon a number of degrees of freedom of the model.

In another embodiment, the method further comprises obtaining a first organ position based upon a first set of representative data images at a specific time, obtaining a second organ position based upon a second set of representative data images at a second specific time; and obtaining a third organ position at a third specific time between the specific time and the second specific time based upon an interpolation between the first set of representative data images and the second set of representative data images. The representative data images may be limited to two dimensions. The method may also further comprise projecting a two dimensional position of the organ from the patient based organ model.

DETAILED DESCRIPTION

An exemplary embodiment of the present invention provides a model of a patient's heart that may be used during evaluative procedures, such as catheter insertion. Aspects of the invention also provide for analysis of other organs so that these organs may also be evaluated, as needed.

Figure 1:
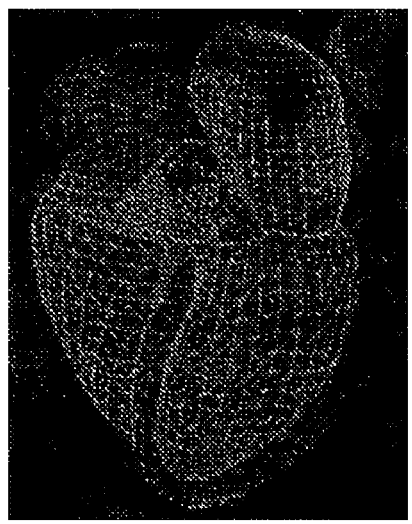
FIG. 1 is a scan of a heart image processed in conformance with an embodiment of the present invention.

In one embodiment, a basic heart model captures the shape and movement of the heart chambers as provided in FIG. 1. The basic heart model closely approximates the true anatomy of the human heart taking into account the differences between various individuals in size, shape and heart muscle movement. The basic heart model properly reflects its interior, including portals of the circulatory system. Other components are added to the model, such as the pulmonary veins.

In an embodiment of the invention, it is possible to obtain information of the geometry of the inner surface of the heart chambers by fitting a database-guided model of the heart to a very limited set of the low-dose rotational acquisitions. First, a model is prepared using an experience based approach wherein a set of classifiers is developed based upon heart structures found in a database. To use this model, a patient is placed in a scanner and low-dose rotation acquisitions are made to obtain the required information. This procedure is called a model-based reconstruction of the heart. The patients heart data is then "reconstructed" using the experience based classifiers previously developed and the scans previously obtained. This dynamic model may be used by a physician during procedures to allow for the insertion of a catheter, for example, as a non-limiting example.

Such reconstructions, based on the certain priors encapsulated in the database, reveal details specific to a given patient, such that catheter navigation is able to be performed successfully.

In an exemplary embodiment of the invention, instead of performing high-dose acquisition data scans on a patient, a short low-dose acquisition is performed rotating the C-arm around the patient and recording only 20-30 images (instead of 300-500). This low dose acquisition is done with ECG synchronization.

The number of images that are acquired depends on the complexity (degrees of freedom) of the database-guided model of the heart. The three dimensional volume reconstruction based on the limited set of projections is, normally, full of artifacts. This defect is overcome, however by using the data obtained to provide a relatively low quality reconstruction that is sufficient to fit the model of the heart.

If needed, one or two more low-dose acquisitions, as above, could be performed at different phases of the heart to better fit the model's kinematics. Therefore, any number of low-dose acquisitions can be conducted on an individual to fill in the necessary data for the model, if such data is needed for purposes of providing a detailed model.

In an alternative exemplary embodiment of the invention, a small number of 2D+t images taken may be sufficient to solve for the kinematics. Once the database-guided model is properly fit, it is used to visualize the inner-surface of the heart chambers for 2d-3d-style navigation.

Any motion of the patient, such as a patient's breathing motion and the natural movement of the beating heart, make a two dimensional-three dimensional overlay of the images with the rigid 3D volume obtained during the CT-scan difficult and inaccurate. The loss of the accuracy can be large that they will significantly limit the usefulness of the method for catheter navigation.

The database-guided model of the heart is used to "interpolate" between the phases of the heart for which the 3D data available. Furthermore, once the model has been fit and registered with the 2D imaging system, the flexing of the heart muscle and the overall movement (breathing motion) can be determined by detection (in 2D images) just a few recognizable features of the heart and measuring their position. The overall silhouette of the heart, which is usually quite visible, can also be used to properly position the model and determine its simulated heart phase.

Figure 2:
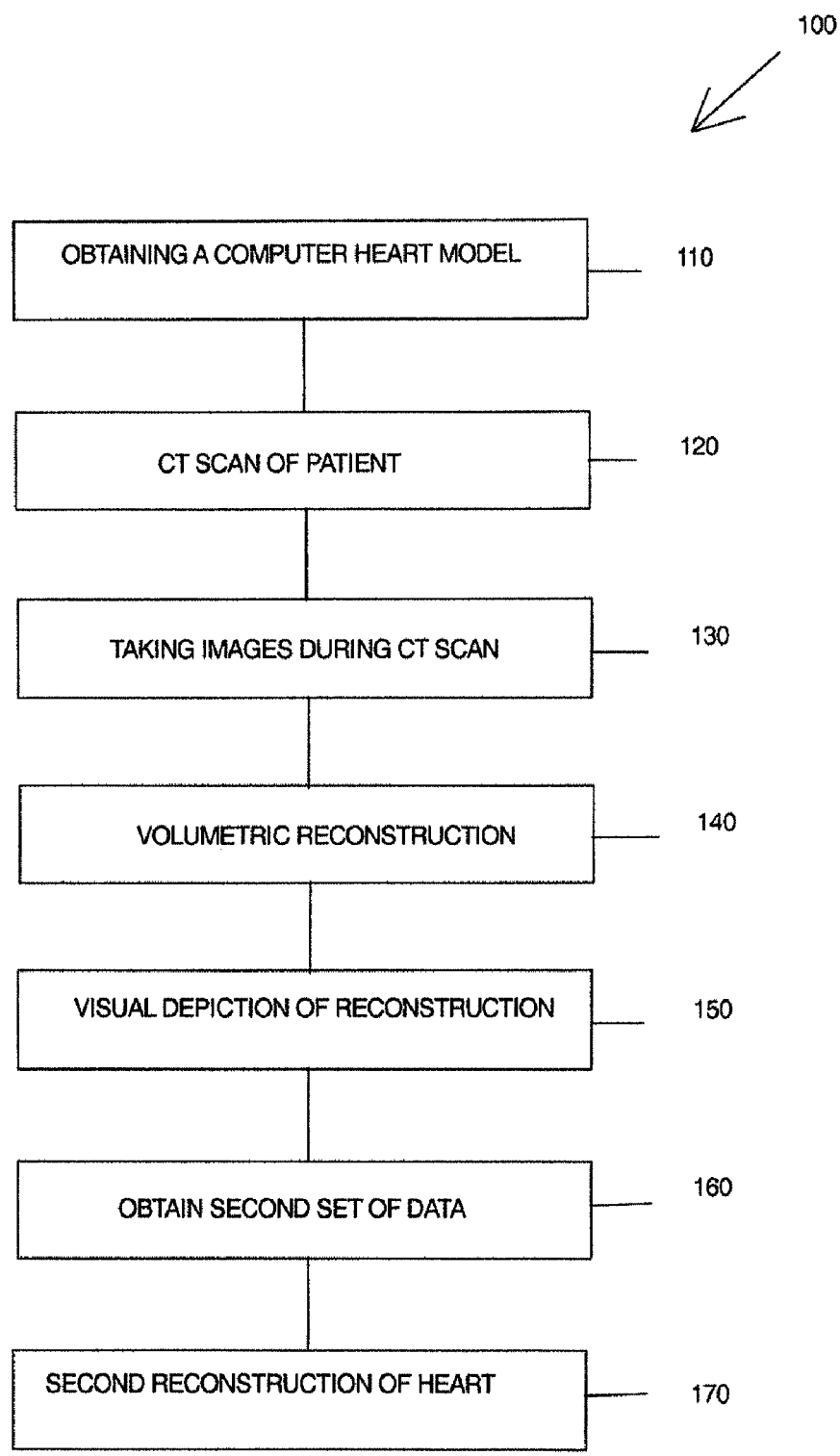
FIG. 2 is a flow chart for a method to use a heart model to evaluate a patient based upon patient data to be used for navigation during medical evaluation.

Referring to FIG. 2, an exemplary method 100 for creating an organ model for a patient is presented that is based upon the previous patients physical characteristics obtained from an experience database. The method 100 entails developing a computer heart model with appropriate classifiers, the computerized heart model having a three dimensional volume data set of classifiers 110. Next, a CT scan, or other scanning technology is performed on a patient by placing the given patient in a scanning device 120. Following this step, representative data images of the patients heart is taken while changing position of the image scan, the data images taken with ECG synchronization 130. Next, a specific heart reconstruction is performed with data from the patient's heart based upon the classifiers 140. The heart model is then visually depicted 150 so that a researcher/medical professional can see the results 150. The results may be used, for example, during catheter navigation. As provided above, a second set of data 160 may be obtained to provide more information needed for the model, if necessary. A second reconstruction 170 may then be performed with the additional information. Successive sets of data may be obtained, followed by reconstructions of the organ in question.

Figure 3:
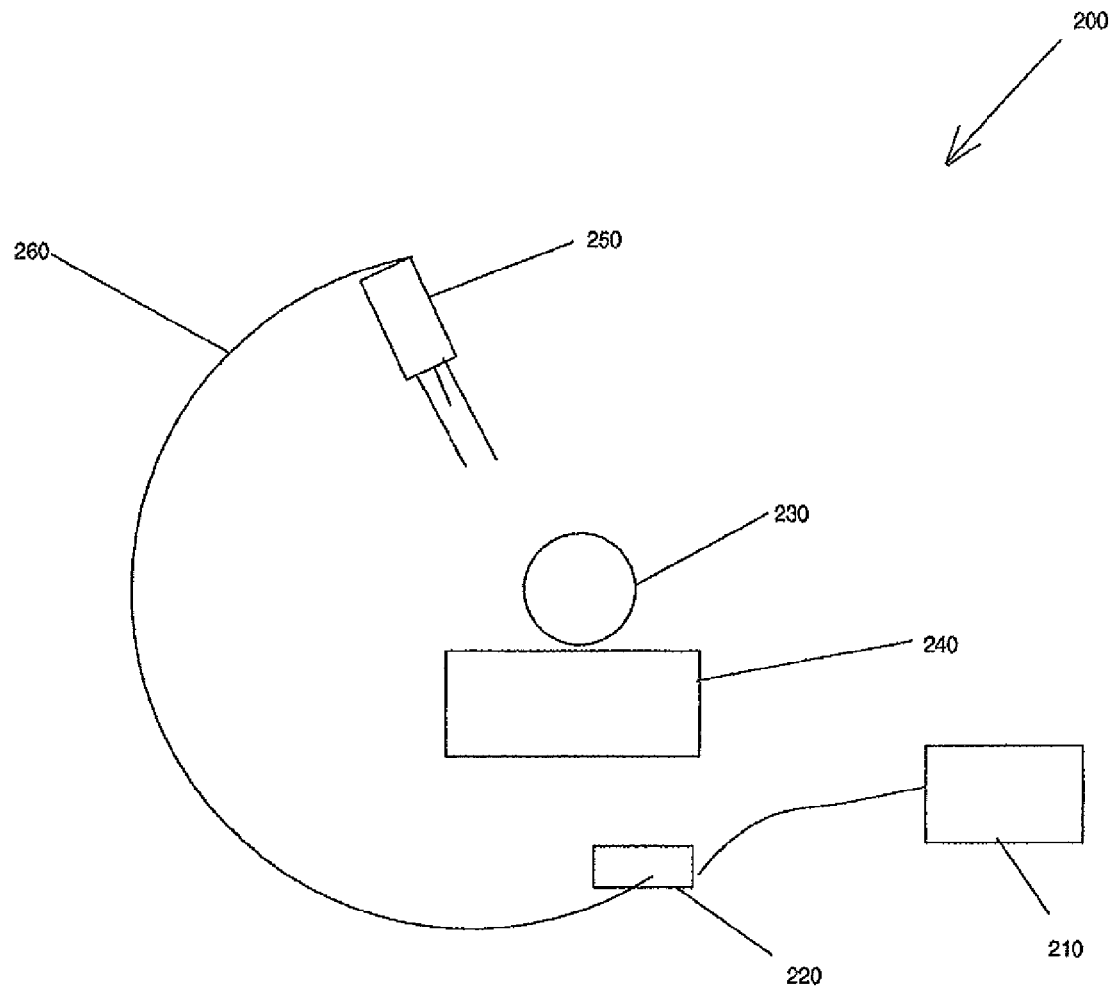
FIG. 3 is an arrangement drawing for obtaining data for construction of a model based organ representation system.

Referring to FIG. 3, an exemplary arrangement 200 for producing a model based reconstruction of an organ of a patient 230 is provided. In this exemplary arrangement, a patient 230 lays on a observation table 240. An arrangement for obtaining data 250, in this case a CT scan device, allows for scanning of the patient 230 while moving a detector 220 on the opposite side of the patient 230. Signals produced by the arrangement 250 are detected by the detector 220 and transmitted to computer 210 that records the signals. The arrangement 250 and the detector 220 travel on a C-arm 260 around the patient 230, thereby allowing detection capabilities around the organ in question. More or less information may be obtained from the patient 230 to refine the model as needed. The arrangement 250 may be an x-ray, CT scan or other diagnostic apparatus. Similarly the C-arm 260 may be any type of apparatus that would allow for scanning over a three dimensional organ of interest. The computer 210 may have a visual output that will allow a researcher to see the model as it is developed.

The motion of the patent, the breathing motion and the natural movement of the beating heart, make the 2D3D overlay of the fluoro images with the rigid 3D volume obtained during the CT-scan or DynaCT difficult and inaccurate in conventional systems. The loss of the accuracy can be so large that it will significantly limit the usefulness of the method for catheter navigation.

The database-guided model of the heart can be used to "interpolate" between the phases of the heart for which 3D data is available. Furthermore, once the model has been fit and registered with the 2D imaging system, the flexing of the heart muscle and the overall movement (breathing motion) can be determined by detection (in 2D images) just few recognizable features of the heart and measuring their position. The overall silhouette of the heart, which is usually quite visible, can also be used to properly position the model and determine its simulated heart phase.

An embodiment of the present invention provides medical professionals with the capability to evaluate a patient's heart. An embodiment of the present invention also provides a medical professional with the capability to evaluate a patient's heart while minimizing potential radiation exposure of the patient. An embodiment of the present invention also provides for accurate representation of a patient's heart while using technology that is adaptable to currently used apparatus by medical professionals.

In the foregoing specification, the disclosure has been described with reference to specific exemplary embodiments thereof. It will, however, be evident that various modifications and changes may be made thereunto without departing from the broader spirit and scope of the invention as set forth in the appended claims. The specification and drawings are accordingly to be regarded in an illustrative rather than in a restrictive sense.

What is claimed is:

1. A method to obtain a patient based organ model from patient data, comprising:
    storing a computerized organ model based upon at least one data set of patients, the computerized organ model having a set of classifiers derived based upon organ structure information in a database and that are used to determine physical parameters of a patients organ;
    in response to a patient being placed in a diagnostic scanner device, taking representative data images of the patients organ while changing position of the image scan, the data images taken with ECG synchronization; and
    preparing the patient based organ model by generating a patient specific reconstructed organ model using the representative data images of the patients organ and the set of classifiers in the computerized organ model.

2. The method according to claim 1, wherein a maximum of representative data images of the patient's organ taken is a smaller number of images compared with a full acquisition and comprise a reduced number of images insufficient for generation of an artifact free full 3D organ model.

3. The method according to claim 1, further comprising:
    visually depicting the patient's organ based upon the representative data images and
    iteratively acquiring additional representative data images of the patient's organ to supplement the patient specific reconstructed organ model in response to user command.

4. The method according to claim 1, further comprising:
    identifying artifacts in the model based upon the representative data images taken.

5. The method according to claim 4, further comprising:
    obtaining a second set of representative data images of the patient's organ while changing position of the image scan, the data images taken with ECG synchronization to eliminate artifacts; and
    preparing a revised patient based organ model by evaluating the second set of representative data images of the patients organ with the set of classifiers in the computerized organ model.

6. The method according to claim 5, further comprising:
    identifying a second set of artifacts in the model based upon the representative data images taken.

7. The method according to claim 5, further comprising:
    obtaining a third set of taking representative data images of the patient's organ while changing position of the image scan, the third set of data images taken with ECG synchronization to eliminate artifacts; and
    preparing a second revised patient based organ model by evaluating the representative data images of the patients organ with the set of classifiers in the computerized organ model.

8. The method according to claim 1, further comprising:
    obtaining a first organ position based upon a first set of representative data images at a specific time;
    obtaining a second organ position based upon a second set of representative data images at a second specific time; and
    obtaining a third organ position at a third specific time between the specific time and the second specific time based upon an interpolation between the first set of representative data images and the second set of representative data images.

9. The method according to claim 1, wherein the representative data images are limited to two dimensions.

10. The method according to claim 9, further comprising:
projecting a two dimensional position of the organ from the patient based organ model.

11. A method to obtain a temporal patient based organ model from patient data, comprising:
obtaining a computerized organ model based upon at least one data set of patients comprising temporal information, the computerized organ model having a set of classifiers derived based upon organ structure information in a database and that are used to determine physical parameters of a patients organ; including motion information;
in response to a patient being placed in a diagnostic scanner device, taking representative temporal data images of a patients organ while changing position of the image scan; and
preparing a temporal patient based organ model by generating a patient specific reconstructed organ model using the representative data images of the patients organ and the set of classifiers in the computerized organ model.

12. A program storage device readable by machine, tangibly embodying a program of instructions executable by the machine to perform method steps comprising:
acquiring data of a computerized organ model based upon at least one data set of patients, the computerized organ model having a set of classifiers derived based upon organ structure information in a database and that are used to determine physical parameters of the patients organ;
in response to a patient being placed in a diagnostic scanner device, acquiring representative data images of a patients organ while changing position of the image scan, the data images taken with ECG synchronization; and
preparing the patient based organ model by generating a patient specific reconstructed organ model using the representative data images of the patients organ and the set of classifiers in the computerized organ model.

13. The device according to claim 12, wherein a maximum of representative data images of the patient's organ taken is 30 images.

14. The device according to claim 13, wherein the method accomplished further comprises:
visually depicting the patient's organ based upon the data images.

15. The device according to claim 13, wherein the method accomplished further comprises:
identifying artifacts in the model based upon the representative data images taken.

16. The device according to claim 15, wherein the method accomplished further comprises:
obtaining a second set of representative data images of the patient's organ while changing position of the image scan, the data images taken with ECG synchronization to eliminate artifacts; and
preparing a revised patient based organ model by evaluating the representative data images of the patients organ with the set of classifiers in the computerized organ model.

17. The device according to claim 13, wherein a maximum of representative data images of the patients organ taken is dependent upon a number of degrees of freedom of the model.

* * * * *